(12) United States Patent
Farnsworth et al.

(10) Patent No.: US 7,828,857 B2
(45) Date of Patent: Nov. 9, 2010

(54) SYSTEM FOR USING A DIGIT TO POSITION A PROSTHETIC OR ORTHOTIC DEVICE

(75) Inventors: Troy Farnsworth, Canyon Lake, TX (US); Michael E. Tompkins, Jamestown, NC (US)

(73) Assignee: Hanger Orthopedic Group Inc., Bethesda, MD (US)

( * ) Notice: Subject to any disclaimer, the term of this patent is extended or adjusted under 35 U.S.C. 154(b) by 0 days.

(21) Appl. No.: 12/027,163

(22) Filed: Feb. 6, 2008

(65) Prior Publication Data

US 2008/0215162 A1    Sep. 4, 2008

Related U.S. Application Data

(60) Provisional application No. 60/888,467, filed on Feb. 6, 2007.

(51) Int. Cl.
*A61F 2/68* (2006.01)
*A61F 2/54* (2006.01)
*A61F 2/48* (2006.01)

(52) U.S. Cl. .......................................... 623/64; 623/24

(58) Field of Classification Search .................. 623/24, 623/25, 57, 63, 64; 901/30
See application file for complete search history.

(56) References Cited

U.S. PATENT DOCUMENTS

| 4,094,016 | A | * | 6/1978 | Eroyan | 623/24 |
| 4,650,492 | A | * | 3/1987 | Barkhordar et al. | 623/24 |
| 4,792,338 | A | * | 12/1988 | Rennerfelt | 623/64 |
| 5,080,682 | A | | 1/1992 | Schectman | |
| 5,888,246 | A | | 3/1999 | Gow | |
| 6,361,570 | B1 | | 3/2002 | Gow | |
| 2006/0155385 | A1 | * | 7/2006 | Martin | 623/24 |
| 2006/0224249 | A1 | | 10/2006 | Winfrey | |
| 2008/0262636 | A1 | * | 10/2008 | Puchhammer | 623/64 |

FOREIGN PATENT DOCUMENTS

WO    WO00/69375    * 11/2000

OTHER PUBLICATIONS

International Search Report and Written Opinion from the International Searching Authority (US) for International Application No. PCT/US08/53209 dated Aug. 7, 2008.

* cited by examiner

*Primary Examiner*—William H Matthews
*Assistant Examiner*—Marcia Hoffman
(74) *Attorney, Agent, or Firm*—Stroock & Stroock & Lavan LLP

(57) ABSTRACT

A method and system for determining a grip or grasp pattern of a prosthetic terminal device or other orthotic device using the position of the thumb or other digit as the initial determination of the grasping function. The system comprising sensors, an electronic control system and a motor drive.

20 Claims, 14 Drawing Sheets

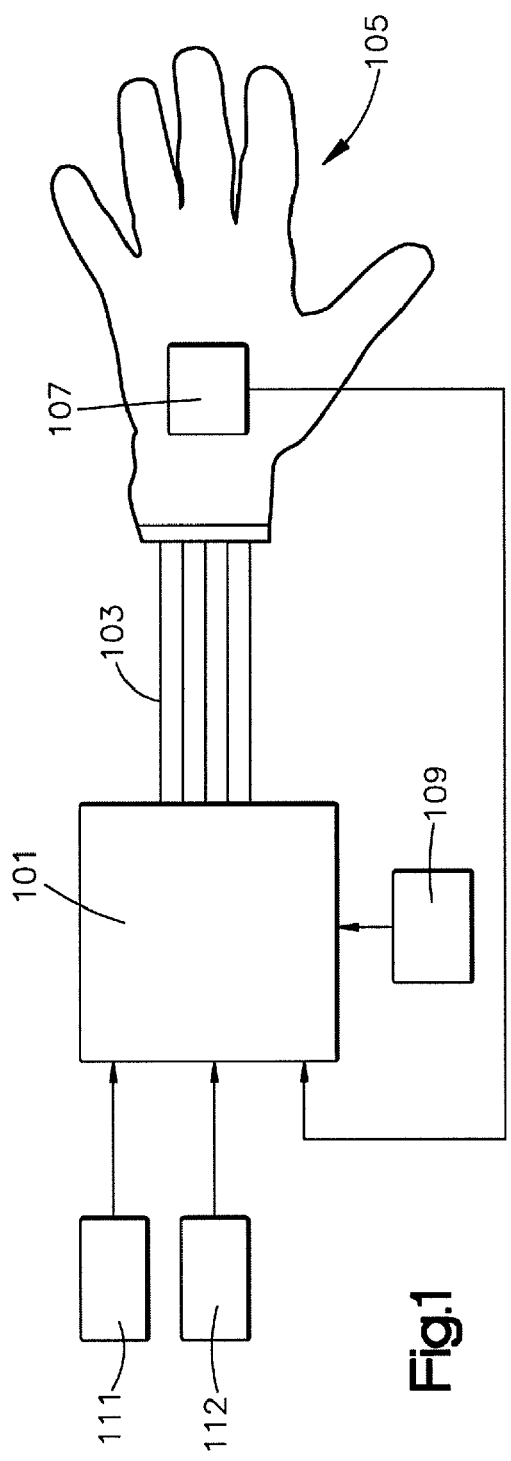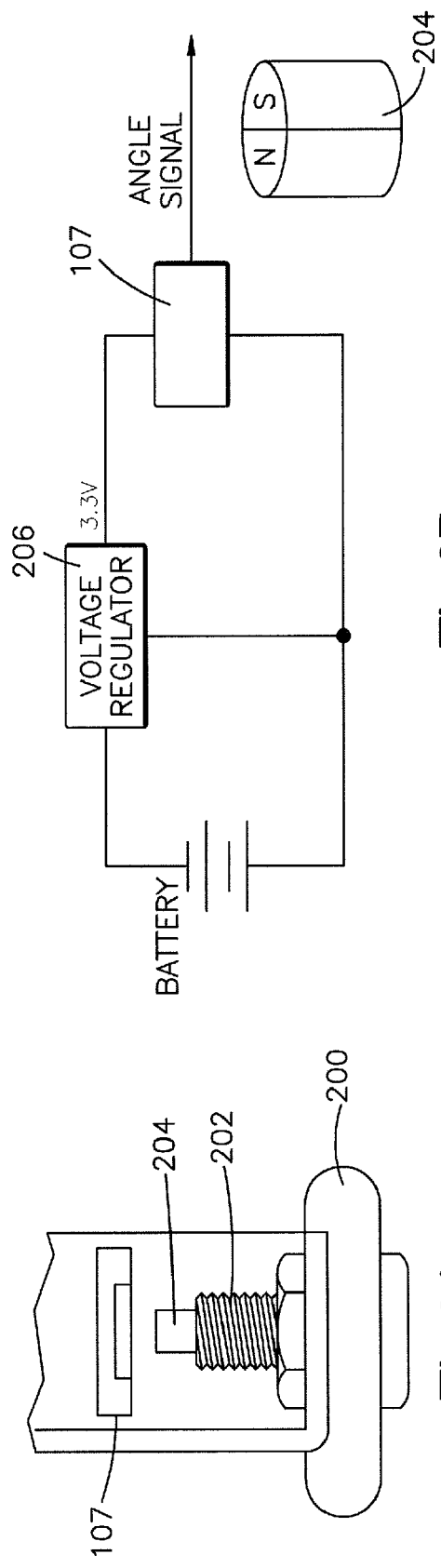

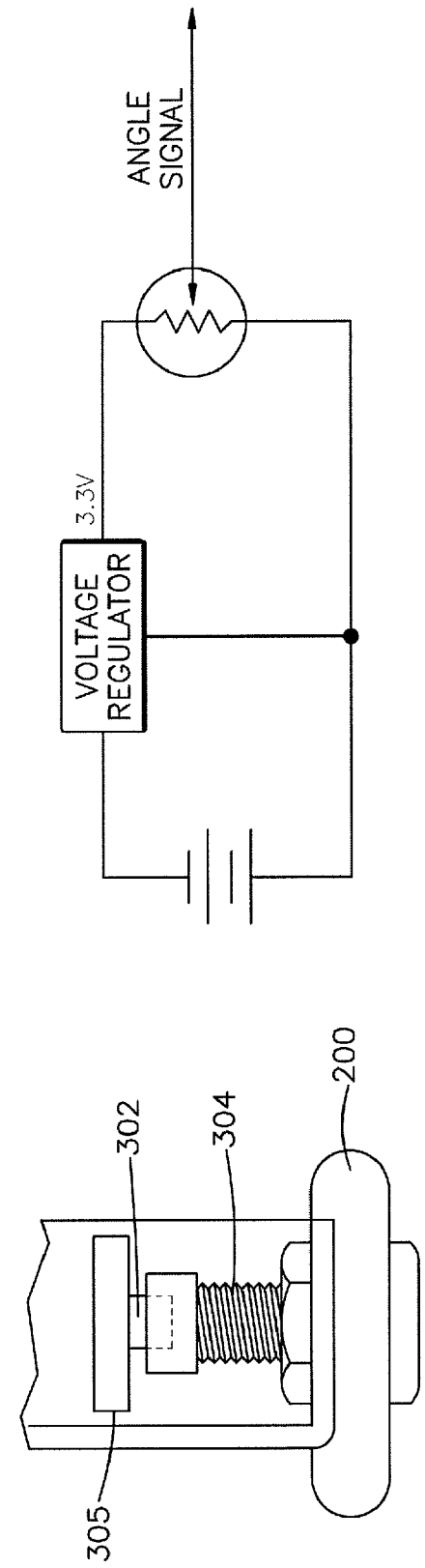
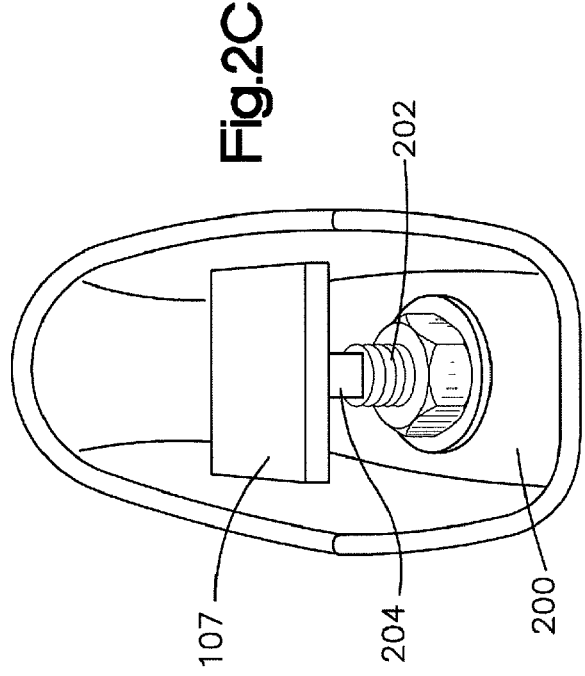

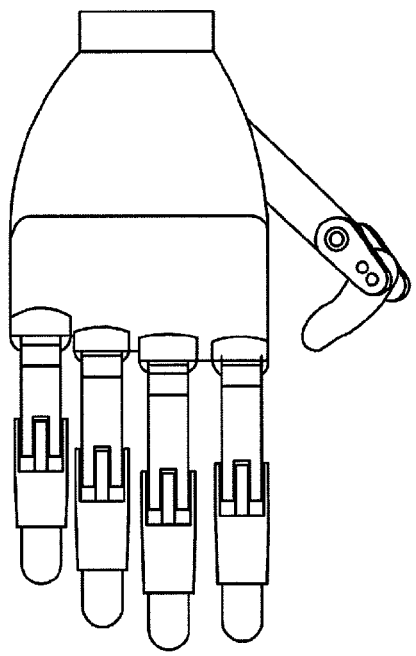
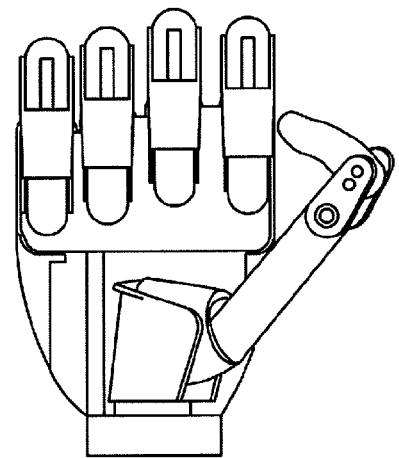
Fig.9A  Fig.9B
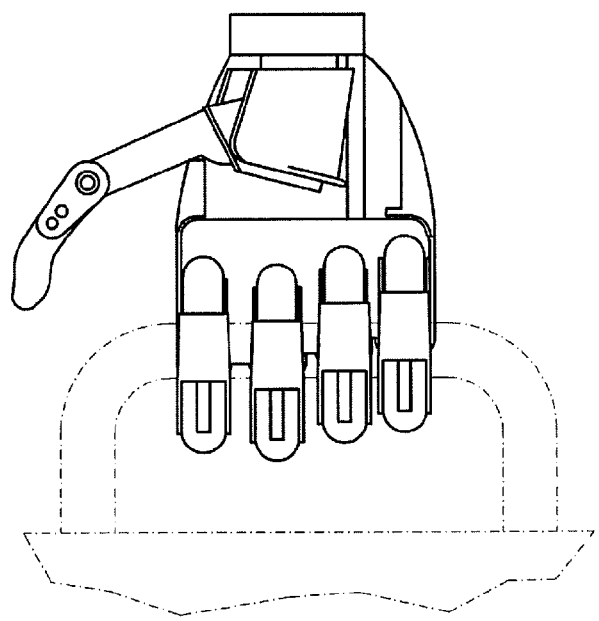
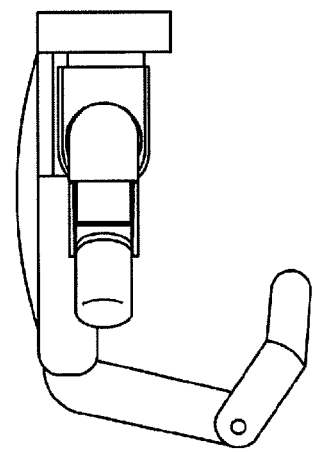
Fig.10A  Fig.10B

SYSTEM FOR USING A DIGIT TO POSITION A PROSTHETIC OR ORTHOTIC DEVICE

CROSS REFERENCE TO RELATED APPLICATION

This application claims the benefit of provisional application Ser. No. 60/888,467 filed on Feb. 6, 2007 entitled "SYSTEM AND METHOD FOR USING A DIGIT TO POSITION A PROSTHETIC OR ORTHOTIC DEVICE", the entire disclosure of which is incorporated herein by reference.

BACKGROUND OF THE INVENTION

1. Field of the Invention

The present invention is generally related to a method and system for determining a grip or grasping pattern of a prosthetic terminal device or other orthotic device using the position of the thumb or other digit as the initial determination of the grasping function.

2. Description of the Related Art

In the field of prosthetics, electrically powered terminal devices such as hands and hooks, have limited functionality, which usually consists of the open and close positions. In general, the thumb, index and middle fingers are mechanically connected together and act in one motion. The ring and pinky fingers are passive and have no gripping capability. These terminal devices do not allow individual movement of the digits. In order to operate the prosthetic devices, the patient typically has one or two control sensors to operate the open and close motion. These are usually configured so that one sensor controls each movement. Such a sensor is usually referred to as a patient sensing device or PSD and may be placed on the forearm of a patient to sense myoelectric signals in the forearm and determine whether to open or close the device. For example one sensor opens the terminal device while a second sensor closes the terminal device.

While the above discussed system works well for terminal devices without individual movement of digits, new electric terminal devices that have individual digit control such as devices that have at least one motor or drive mechanism per digit, pose new challenges to the control system and the patient interface. Since such a device uses multiple digits in multiple positions, this type of terminal device could be positioned in an infinite number of positions. While this new terminal makes the movements more robust than previous devices that limit movement to certain limited positions, it provides difficulties in using the existing two sensors to get accurate information from the patient to determine the exact position requested from the vast array of positions now available. In order to control such devices, additional sensors have been used to monitor the patient's myoelectric signals in order to more accurately calculate the proper movements of the terminal device or its parts. Since more control from the patient is required, this means adding many sensors or complex control systems to interpret the patients' desired action. This is both cumbersome and inconvenient to the patient as well as more complex from an electrical perspective resulting in more errors in controlling the device.

It would therefore be desirous to have a system and method of controlling a prosthetic device using a limited number of sensors while still allowing the patient the flexibility of choosing a number of different actions for the prosthesis.

SUMMARY OF THE INVENTION

In view of the above discussion and the shortcomings in the prior art, the invention seeks to overcome such shortcomings of the prior art by using an electronic or electromechanical digit or thumb sensor connected to the prosthetic or orthotic device to position such prosthetic or orthotic device so that subsequent control signals from the patient will control the terminal device from that established position.

Analysis of the most used gripping patterns or positions of a prosthetic terminal device or other orthotic device has indicated that the thumb position is an appropriate indicator of which gripping patterns are most likely to be performed or desired from that position.

For example, studies have shown that, when the thumb is in its furthest position from the palm, it is usually an indication that the patient wishes to perform certain functions including, but not limited to, a lateral pinch (e.g., to grasp something), hook grip (e.g., to pick something up) or typing with a single finger (e.g., on a keyboard or telephone pad).

When the thumb is in a slightly less abducted position approximately thirty degrees closer towards the palm than when fully abducted, it is an indication that the patient wants to perform certain other functions such as a trigger movement (e.g., to use a drill or firearm), point (e.g., point at an object) or grasp a spherical object (e.g., hold a ball).

When the thumb is in an even less abducted position, approximately sixty degrees closer to the palm than the furthest position, it indicates that the patient wants to use the thumb and index finger to, for example, focus on the tip of an object (e.g., touch the tip of a pencil) or to grip an object in an action position (e.g., hold a pencil or an eating utensil).

When the thumb is closest to the palm of the prosthetic hand, it indicates that the patient is desirous of grasping a cylindrical object (e.g., a water bottle) or a tighter hook grip (e.g., to grasp something to lift and close the palm around such object).

By using the above discussed methodology, the array of gripping patterns or positions can be sub-classified by the position of the thumb. Therefore, by determining the position of the thumb, an electronic control system can more easily determine what position the terminal device needs to be in to perform such actions and move the finger and/or fingers accordingly. In other words, rather than having an infinite amount of digit positions, the position of the thumb will reduce the useful actions to a lesser amount which can be more easily controlled by the patient.

According to one embodiment of the present invention, a sensor is attached to a thumb of a prosthetic device. The thumb sensor comprises an electronic or electromechanical device that indicates the relative position of the thumb and emits an indication signal. This indication signal is sent to a control system which interprets the thumb angle or position and then moves the thumb of the terminal device to the appropriate position based on the thumb position. The control system then monitors the patient signals emitting from the patient sensors for example to determine the movement of the other digits while the thumb is in its current position.

In yet other embodiments, positions or movements of other digits other than the thumb and even movements of a patient's real limbs or other digits can be used to effectuate the movement of the prosthetic device.

BRIEF DESCRIPTION OF THE DRAWINGS

A further understanding of the present invention can be obtained by reference to the embodiments set forth in the illustrations of the accompanying drawings wherein like reference numerals refer to like components. The drawings are not necessarily drawn to scale and are not in any way intended to limit the scope of this invention, but merely to clarify the illustrated embodiment of the invention.

FIG. 1 is a diagram showing a terminal device having a thumb angle sensor according to an embodiment of the present invention;

FIG. 2A shows an exploded view of a thumb angle sensor according to one embodiment of the present invention;

FIG. 2B shows a magnet and sensor is as a circuit diagram assembly according to an embodiment of the present invention;

FIG. 2C shows an enlarged picture of a thumb angle sensor according to an embodiment of the present invention;

FIG. 3A shows an exploded view of a thumb angle sensor according to an embodiment of the present invention;

FIG. 3B shows a potentiometer sensor according to an embodiment of the present invention;

FIGS. 8-11 show different finger positions according to other embodiments of the present invention;

DETAILED DESCRIPTION OF THE PREFERRED EMBODIMENTS

Figure 5:
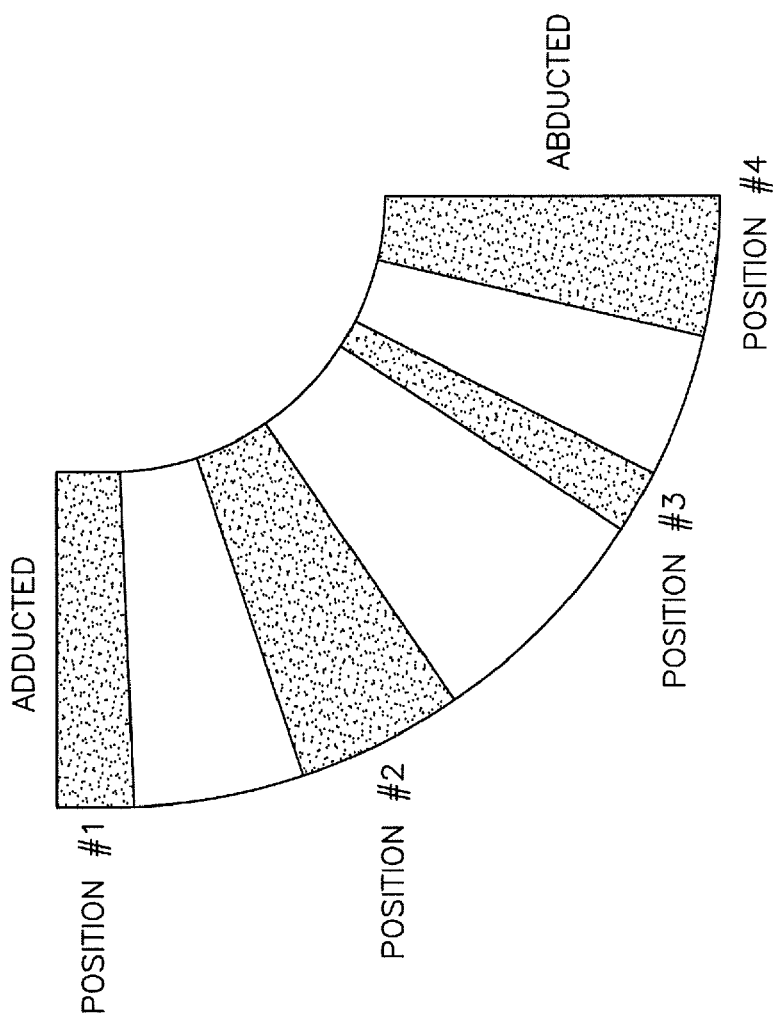
FIG. 5 shows different thumb positions according to an embodiment of the present invention.
Figure 4A:
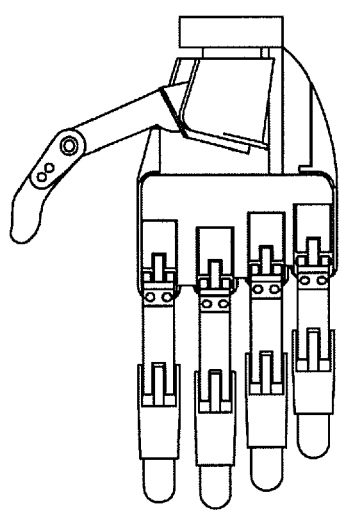
FIG. 4 shows a thumb sensor according to an embodiment of the present invention.
Figure 4B:
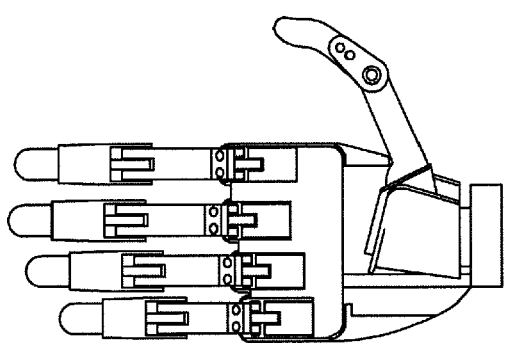
Figure 6D:
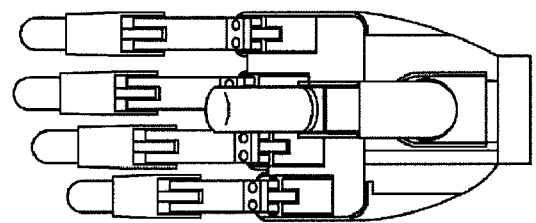
FIG. 6 shows different thumb positions according to an embodiment of the present invention.
Figure 6C:
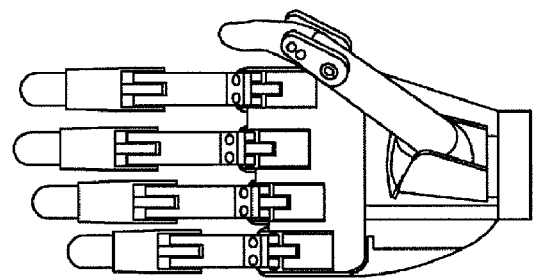
Figure 6B:
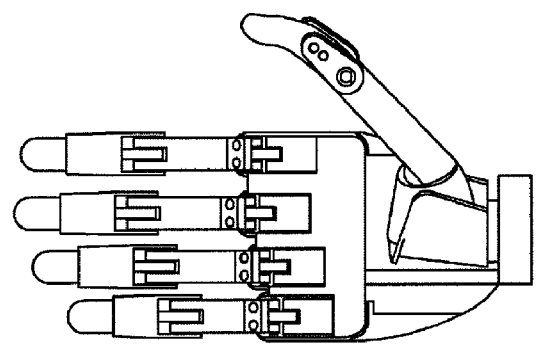
Figure 6A:
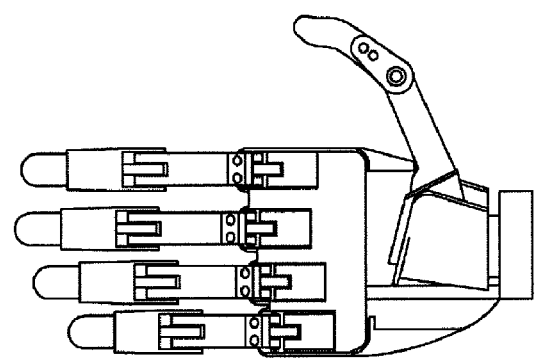
Figure 8:
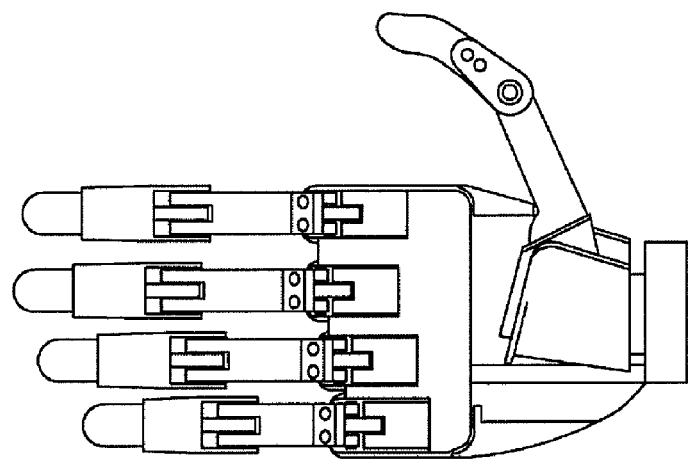

With reference to FIGS. 1-21, an electronic sensor device according to a preferred embodiment of the present invention will be described in detail below. Though the preferred embodiment is described in the context of a terminal device that can individually and independently move each digit, the present invention could be used in other contexts in which a device is connected to a patient's body. For example, the device could be an artificial arm, an orthotic component, or other past, current or future prosthetic and orthotic products. An orthotic device that aids the patient in gripping could be positioned using feedback from a sensor or an individual switch. The use of a prosthetic hand is merely an illustrative embodiment and should not and does not limit the breadth or full scope of the present invention in any way.

As can be seen in FIG. 1, an Electronic Control System 101, as is known in the art, is connected to a motor drive 103 that is connected to a prosthetic device 105. The Electronic Control System can be any processor and/or other circuit board that is capable or receiving a signal and translating such signal to manipulate a motor drive. The Electronic Control System preferably contains an analog to digital converter that can convert the analog signal received into a digital signal. In the present embodiment, the prosthetic device 105 is a hand and contains a thumb angle sensor 107, which is discussed in greater detail below, and which senses the movement of the thumb of the prosthetic device and emits a signal based on the position of the thumb. The signal that is emitted from the thumb angle sensor is fed as an input signal into the electronic control system 101, which is preferably powered by a battery 109. The sensor 107 is also preferably powered by the system power which would typically be battery 109, although other power systems could be provided without departing from the spirit of the invention.

The patient who is controlling the prosthetic device preferably has any number of sensors attached to him or her to sense their muscle signals. Preferably there are only two sensors attached to the patient as shown in FIG. 1. These patient sensors 111 and 112 are preferably Electromyographic ("EMG") sensors as is known in the art, and are preferably placed on both sides of a patient's forearm to receive muscle signals that indicate the patient's muscle movement. One example of an EMG sensor is the Otto Bock brand of myographic electrode, from Otto Bock, Two Carlson Parkway North, Suite 100, Minneapolis, Minn. 55447-4467, model number 13E200.

In the present embodiment, only two sensors are necessary to carry out the movements desired by the patient. Once the patient sensors 111 and 112 sense these signals, these signals are fed into the electronic control system 101. In the scenario where EMG sensors are used, these signals can be an open signal, closed signal or a co-contraction of the signals as is known in the art. Alternatively, the signals can be fed into the electronic control system by other input means either directly entered by the patient or sensed from the patient in differing manners as is known or may become known in the art. As will be discussed in more detail below, based on the movement of the thumb, the electronic control system is able to process the signals received from the patient to determine the required movement of the prosthetic device 105. For example, if the thumb sensor senses that the thumb is at a position that is furthest abducted from the palm of the hand, a signal will be sent back to the electronic control system 101 indicating such signal and the remaining fingers will be moved to a position enabling the grasps that are indicative of that thumb position as will be discussed below. The patient sensor signals 111 and 112 or other input device will then be read by the electronic control system 101 to determine which of the grasps is appropriate for the patient and the digits will be moved accordingly. As can be seen from this example, the use of the thumb sensor dramatically narrows the array of positions and grips that the prosthetic device will need to be prepared to take and therefore, less input from the patient (and thus less patient sensors) are necessary to determine the exact movement to be taken.

FIG. 2A shows the base of the prosthetic device 105 according to one embodiment of the present invention. As can be seen in FIG. 2A, an axis bolt 202 is fixed to the base of the hand 200 and is stationary regardless of the movement of the hand. Directly on top of the axis bolt 202 is a split magnet 204 that has both a north and south pole on each end of the magnet. This magnetic field of this magnet is used by sensor 107 to determine the rotation and/or axis of the thumb or other digit. To effectuate this, above the magnet is angle sensor 107 that is able to determine the movement of the thumb or other digit based on the change in the magnetic field of magnet 204.

As is shown in FIG. 2B, the sensor electronics which are preferably mounted on a circuit board convert the magnetic field from magnet 204 to a voltage corresponding to the magnetic field position. An on board regulator 206 provides the regulated voltage to provide a relationally constant signal and reduce sensor noise. A volt output (e.g., 3.3 volts) from a voltage regulator is preferably used to power the sensor. The preferred low-noise voltage regulator is a Linear Technology Corp. LT1615. The sensor 107 converts the magnetic field preferably using an angle sensor that is able to sense the sine and cosine of the magnetic field of split magnet 204 to output a signal indicating the x and y coordinates of the thumb to the electronic control system 101 which indicates the angle of the thumb or other digit.

The voltage signal is then input to the Analog to Digital (A/D) converter in the Electronic Control System 101 for converting the varying thumb signal to a digital number representing the thumb angle value. This value is then used by the electronic control system to determine the movements that may be necessary desired or appropriate for the prosthetic device based on such a thumb position.

The angle sensor 107 is preferably a hall-effect magnetic type. The sensor could be selected from any suitable type of sensors known in the art, magnetic or otherwise, but is preferably the TESLA3 manufactured by Asahi Hasei Co. Ltd. of Tokyo Japan. The magnet 204 is preferably part number 55B0081 manufactured by Adams Engineered Products of Elizabethtown, Ky. in the most preferred embodiment.

FIG. 2C depicts an exploded view of the thumb sensor of FIG. 2A is shown, illustrating the sensor 107, magnet 201, bolt 202 and hand base 200.

FIG. 3A shows the base of the prosthetic device according to another embodiment of the present invention. As can be seen in FIG. 3A, instead of an angle sensor and a magnet, a potentiometer 305 can be used to send a signal to electronic control system 101 to indicate the angle of the thumb or other digit. As is seen in FIG. 3A, a potentiometer shaft 302 that moves together with the rotation of the thumb is shown. This shaft is coupled to the axis bolt 304, which, similar to the embodiment discussed above in reference to FIG. 2, is fixed to the hand base and does not move with the rotation of the thumb or other digit.

As can be seen in FIG. 3B, similar to the sensor described above with reference to FIG. 2, the potentiometer sends the angle signal to the electronic control system 101 that uses such signal to determine the universe of movements that the prosthetic device will be able to perform based on the thumb position.

The use of the thumb position sensor to control the positioning of the prosthetic device will now be described in more detail with reference to FIGS. 4-21. The thumb of the prosthetic device can rotate around a center axis. As was discussed above, the position of the thumb is then sent to the electronic control system to determine which further positions of the other digits on the prosthetic device are appropriate based on the thumb position. As seen in FIG. 6, there are four thumb positions along the center axis that start from Position 1 which is being fully abducted away from the palm centerline to Position 4 which is the furthest abducted toward the palm center line. In order to activate the prosthetic device to "grasp" something, the patient or other user rotates the thumb to one of the four positions shown in FIG. 6. Once the thumb has reached one of the four recognized positions, a signal is transmitted from the thumb sensor 107 to the electronic control system 101. This signal is used as the primary input for the electronic control system and allows the electronic control system 101 to operate the motor drive 103 and control the prosthetic device in according with the details set forth below.

Figure 7:
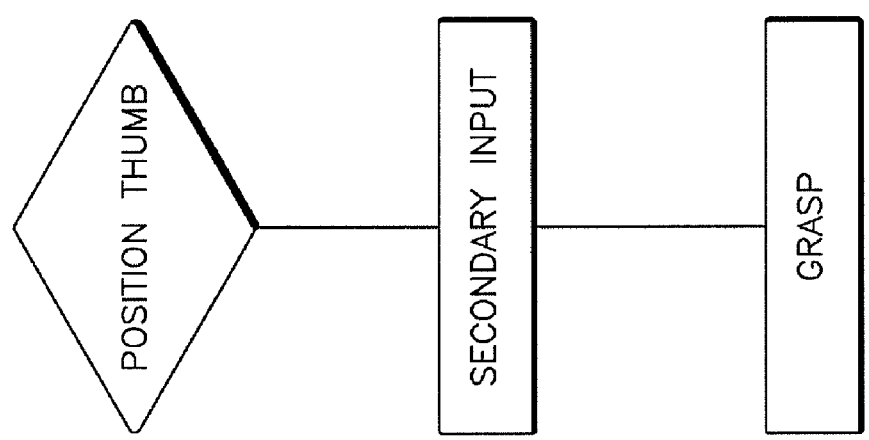
FIG. 7 shows the positioning of the thumb according to an embodiment of the present invention.

If the only digit that needs to be activated is the thumb, the input from the thumb sensor is all that is necessary to effectuate that position. If however additional use of the other digits is necessary, additional input is necessary from, for example, EMG signals that are created from the patient sensors 111 and 112 that are connected to the patient. Alternatively, these inputs can come for example from non-EMG input such as pull or push switches, Force Sensing Resistors ("FSR"), or suspension harnesses or other manners that are known in the art. As shown in FIG. 7, the position of the thumb is combined with the secondary input which can be in the form of EMG signals or non-EMG devices as is known in the art. The electronic control system 101 then uses at least these two variables to determine the proper "grasp" position.

In one embodiment of the present invention, as is shown in FIGS. 8-11, "Position 1", or in other words the furthest position abducted from the palm center, is an indication of either 1) a lateral pinch, 2) a hook grip with the thumb abducted or 3) a single finger typing by the user. Once the electronic control system receives the signal from the thumb sensor that the thumb is in Position 1, it is evident that one of these positionings is desired or required. The electronic control system then looks for input from the patient sensors or other input device to determine which of the positionings is appropriate. As can be seen in FIG. 9, if the signal from the patient sensors (or other input mechanism) indicates that a lateral pinch is desired the electronic control system operates the motor drive to flex and/or extend the finger and/or fingers based on the needs of the user. Alternatively, as can be seen in FIG. 10, if the input to the electronic control system from the patient sensors or other input mechanism indicates that a hook grip with the thumb abducted is being requested by the patient, the electronic control mechanism operates the motor drive to curl the fingers towards the palm, thus enabling the hook grip. Since in the hook grip it is no longer necessary for the thumb to be used the control for the thumb can be deactivated and the user still has control over the other fingers to tighten or loosen the fingers as necessary.

Figure 11A:
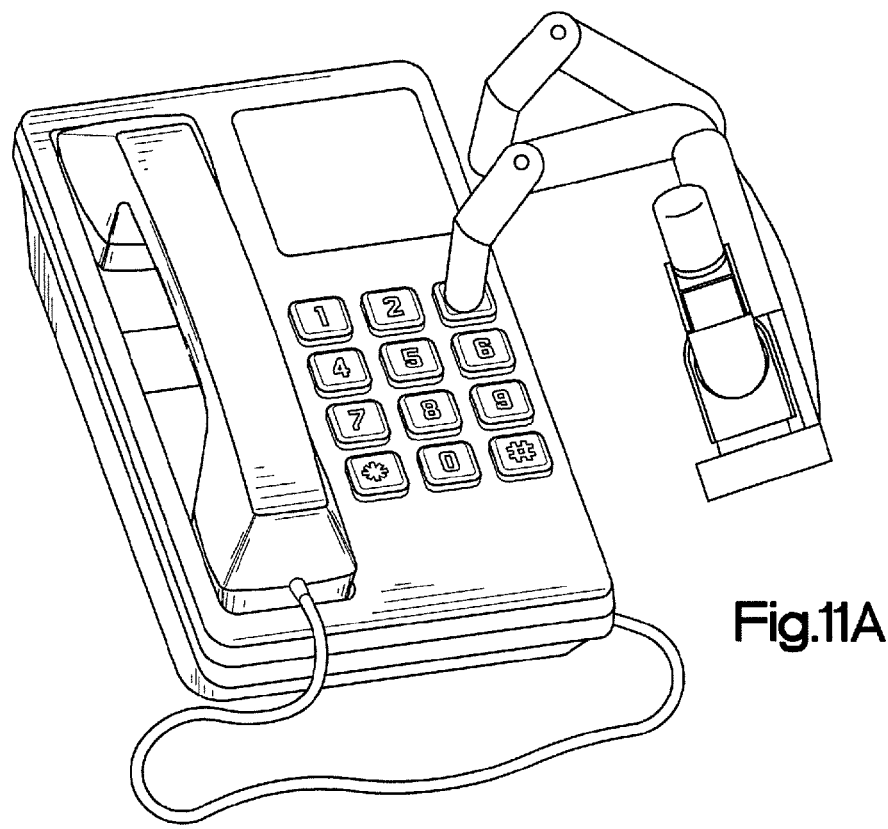
Figure 11B:
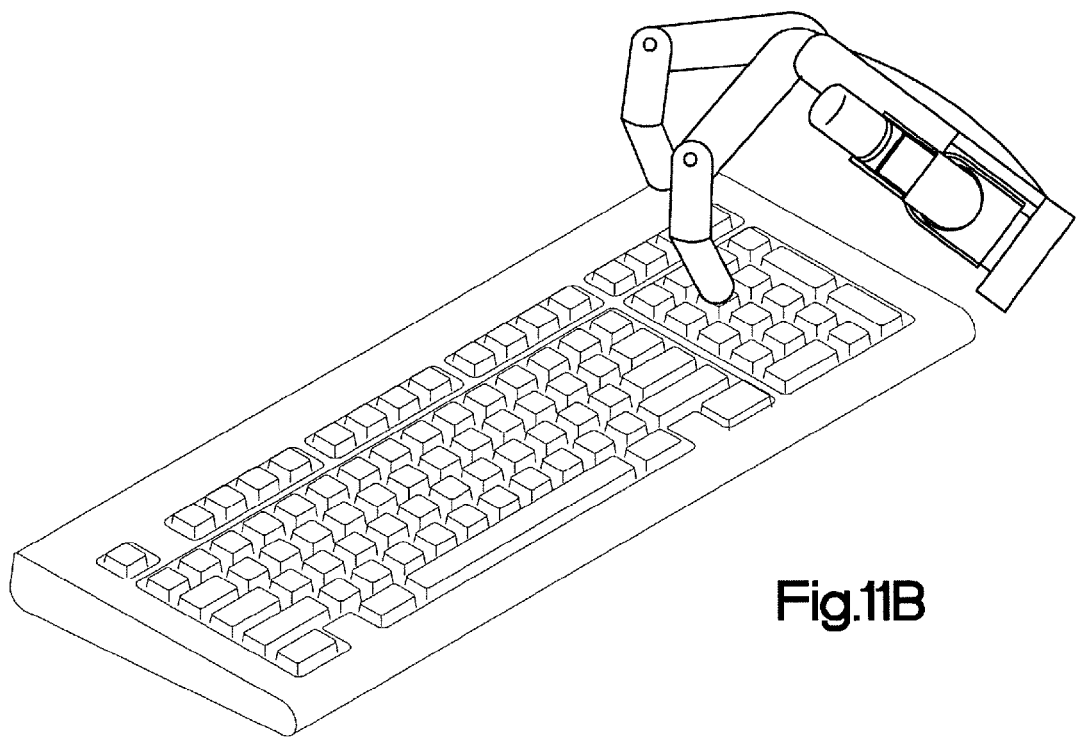

Conversely, as can be seen in FIG. 11, if the input to the electronic control system indicates that the user desires to type with a single finger as for example on a keyboard or telephone, the electronic control system activates the drive motor to move the index finger to a pointing position and deactivates the remaining fingers. The user is then free to use the index finger and type or perform a similar function with such finger.

In another embodiment of the present invention, as is shown in FIGS. 12-15, "Position 2", or in other words a position that is approximately thirty degrees more towards the palm center than Position 1, is indicative of a desire by the user to attain a grip pattern for 1) a trigger; 2) pointing; or 3) grasping a spherical object. Once the electronic control system 101 receives the signal from the thumb sensor that the thumb is in Position 2, the system can determine that one of these positionings is being requested. If the user wants to use the device in this original position without any further movement or use of the other fingers, no additional input is necessary. If a different position is to be used, the electric control system 101 receives additional input form the patient sensors or other input mechanism.

Figure 13B:
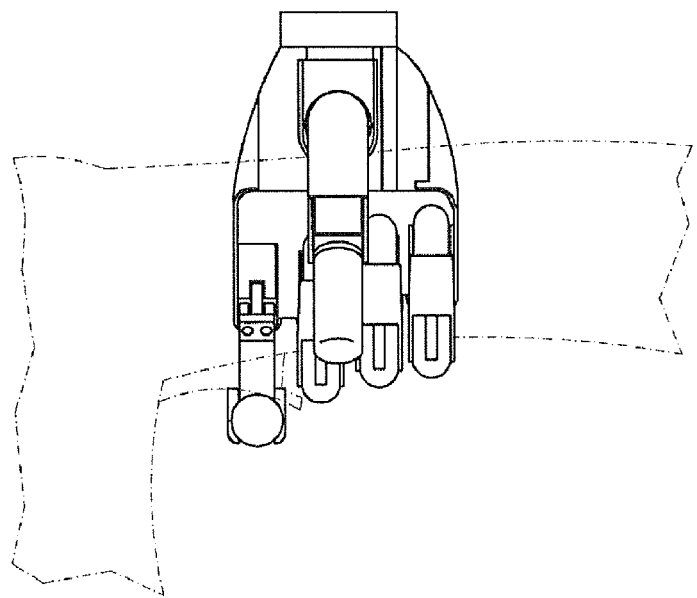
FIGS. 12-15 show different finger positions according to other embodiments of the present invention.
Figure 13A:
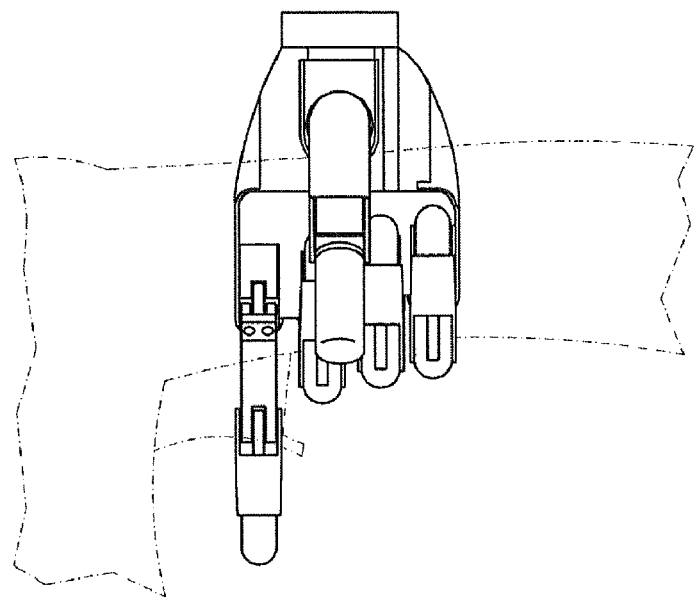
Figure 12:
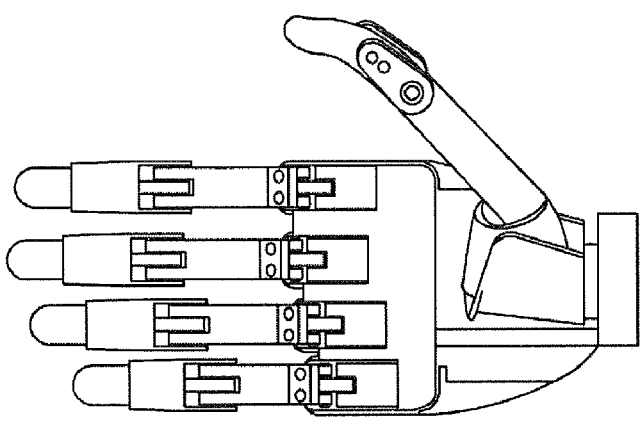
Figure 14A:
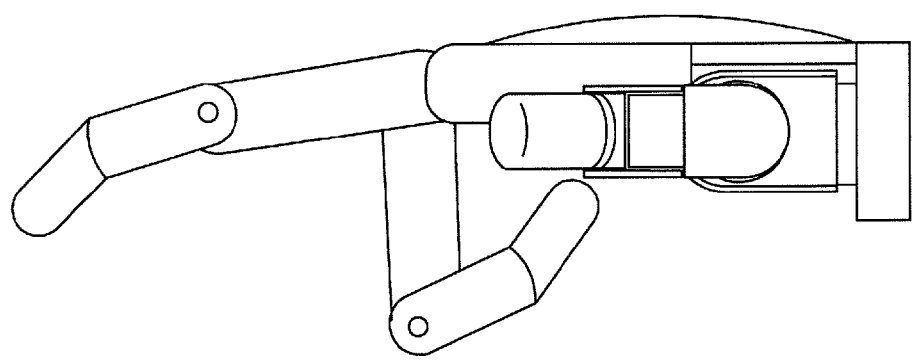
Figure 14B:
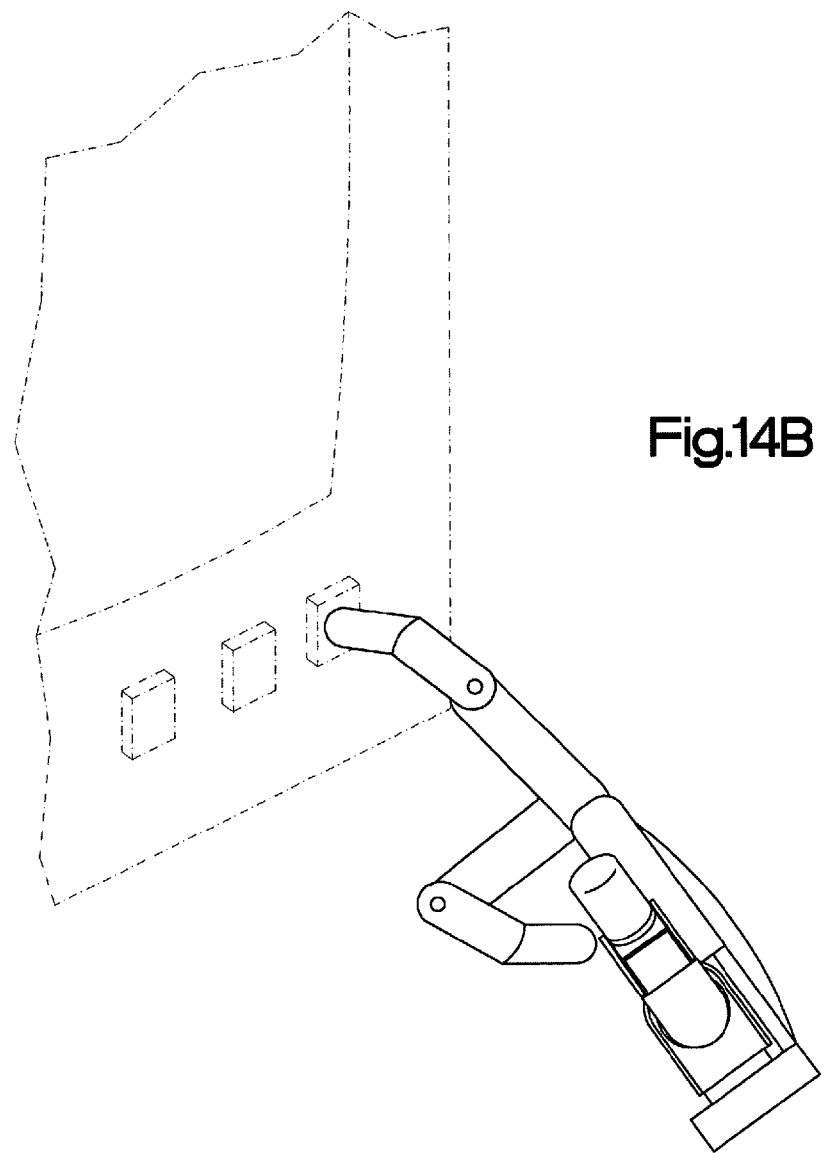

If a trigger grasp is indicated as shown in FIG. 13, the electronic control system enables the motor drive to temporarily suspend the index finger while the other four fingers are closed to grasp around the object (e.g., a drill). Once the object has been grasped, control is transferred back to the index finger for use in the triggering. If however the patient sensors indicates a request from the patient sensors to point, all of the fingers other than the index finger are flexed inward creating an ability for the user to point using the index finger. Similar to the single typing position of Position 1, the user has use of the index finger, however in this situation, the index finger is more positioned to point to an object rather than to use the index finger.

Figure 15B:
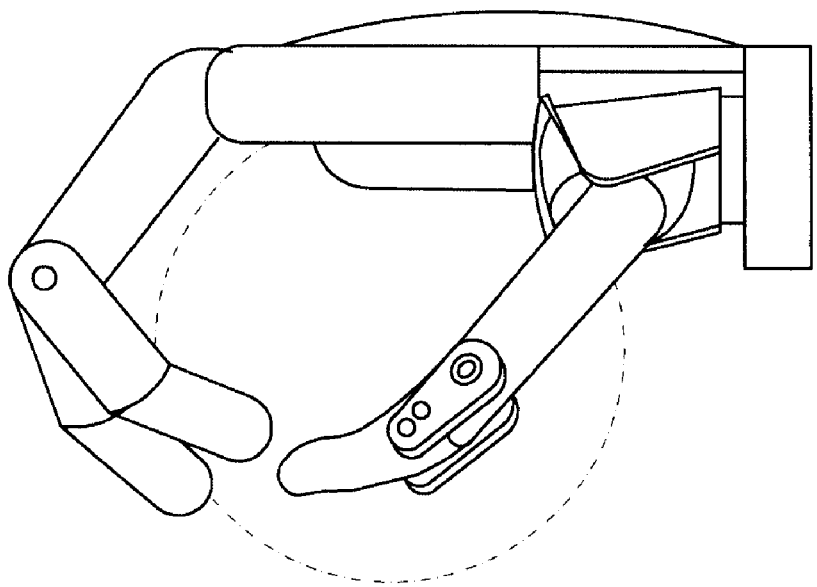
Figure 15A:
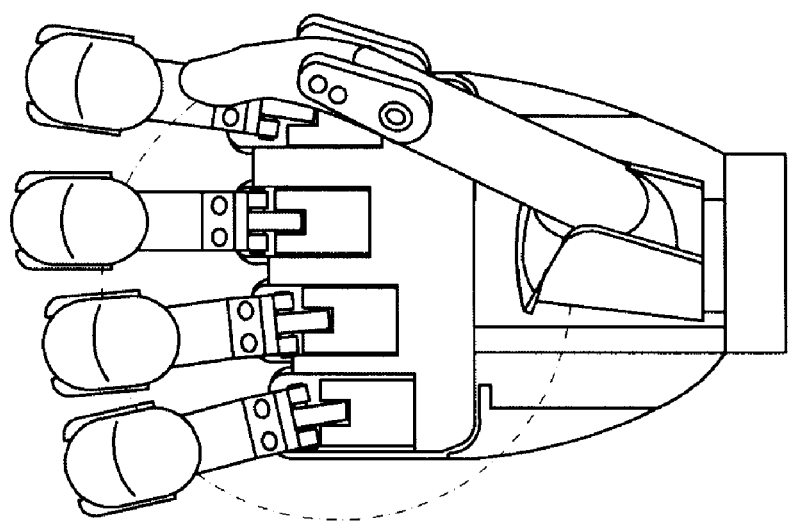

Conversely, as shown in FIG. 15, if the inputs from the user indicates a desire to grasp a spherical object (e.g., a ball), the electronic control system transfers control over all of the fingers to the user to extend or flex the fingers to grasp or release the object. In this situation, the thumb in Position 2 is already positioned to grasp the spherical object and/or release such object as necessary.

Figure 17B:
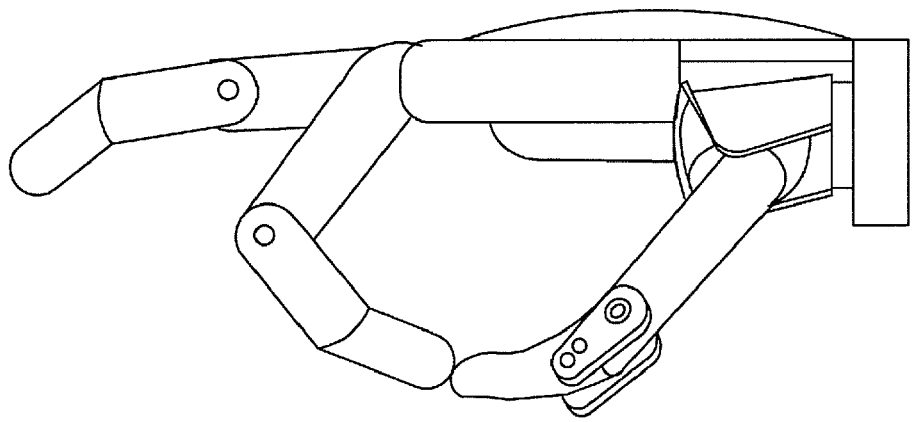
FIGS. 16-18 show different finger positions according to other embodiments of the present invention.
Figure 17A:
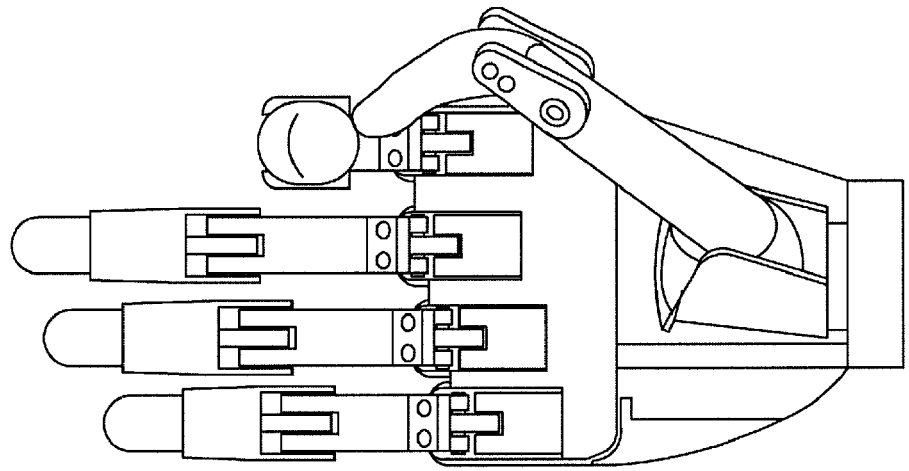
Figure 16:
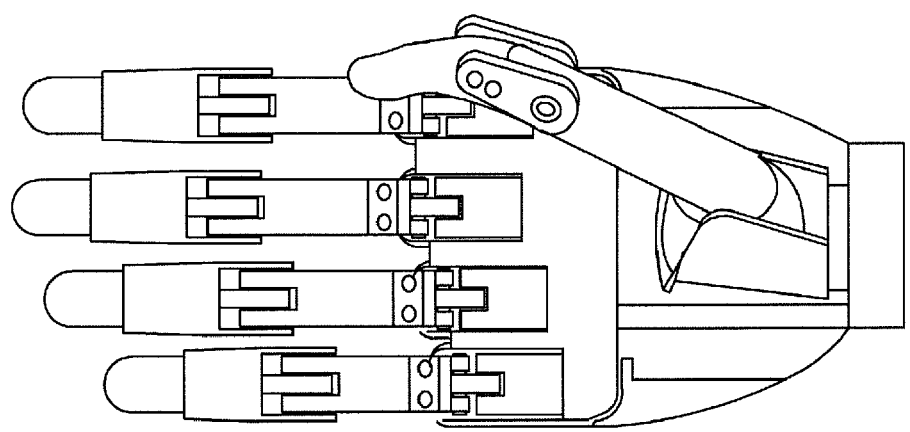
Figure 18B:
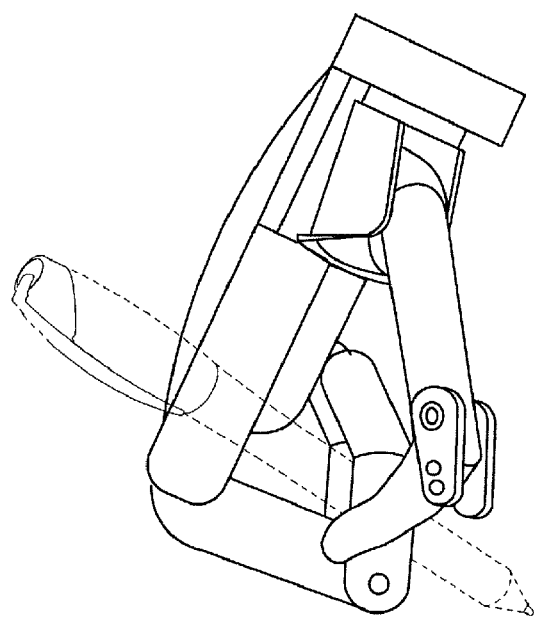
Figure 18A:
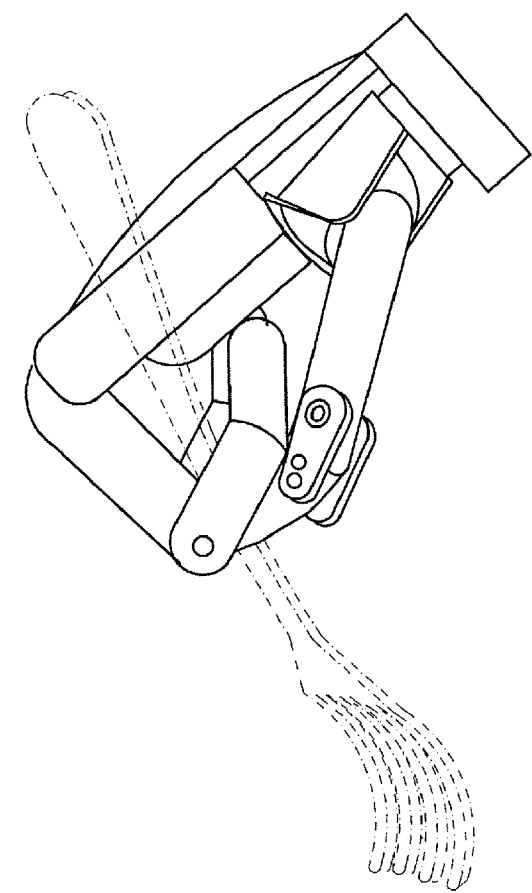

In another embodiment of the present invention, as is shown in FIGS. 16-18, "Position 3", or in other words a position that is approximately sixty degrees more towards the palm center than Position 1, is indicative of a desire by the user to attain a grip pattern for 1) touching a tip object; or 2) grasping a pencil like object. Once the electronic control system receives the signal from the thumb sensor that the thumb is in Position 3, the system can determine that one of these positionings is required. The electronic control system then looks for input from the patient sensors or other input device to determine which of the positionings is appropriate. As can be seen in FIG. 17, if the electronic control system receives input that indicates that the user desires to use a "tip" grasp, the electronic control system effectuates the motor drive to give the user control of the index finger and thumb to move those two fingers closer or further apart from each other. Since the remaining three fingers are not necessary for this use of the hand, they are deactivated and the user can focus on using the thumb and index finger to carry out this action. If on the other hand the input from the user indicates that the user is desirous of grasping a pencil or eating utensil for example as can be seen in FIG. 18, the electronic control system controls the motor drive to preposition the middle ring and pinky fingers into a closed or flex position. The user then controls the index finger to secure the object in place. At that point the user can move the thumb to grasp around the object and create a tight fit.

Figure 20B:
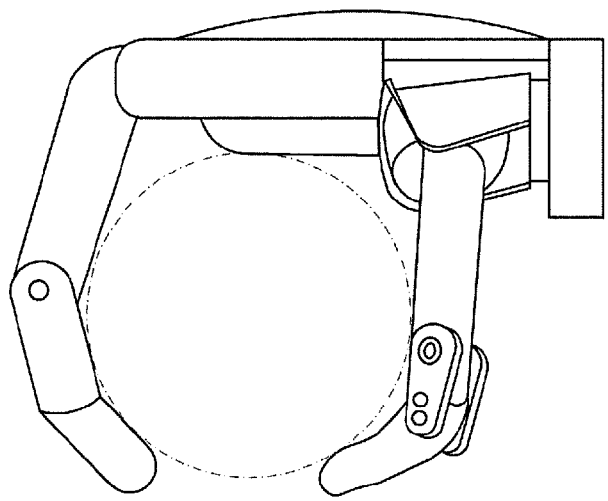
FIGS. 19-21 show different finger positions according to another embodiment of the present invention.
Figure 20A:
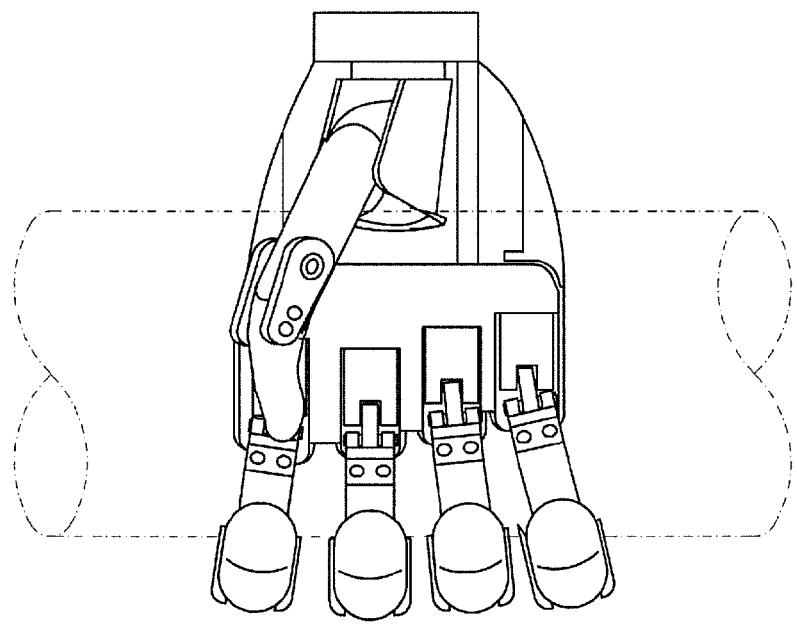
Figure 19:
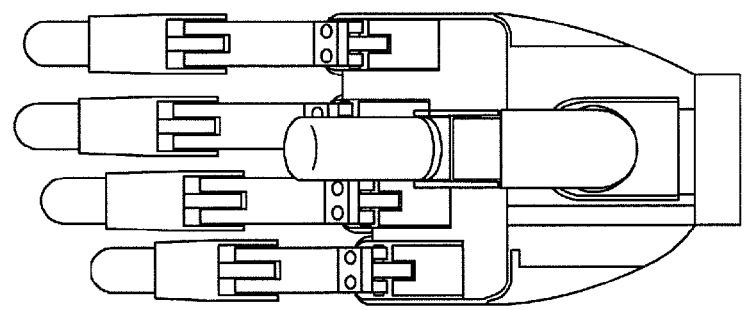
Figure 21B:
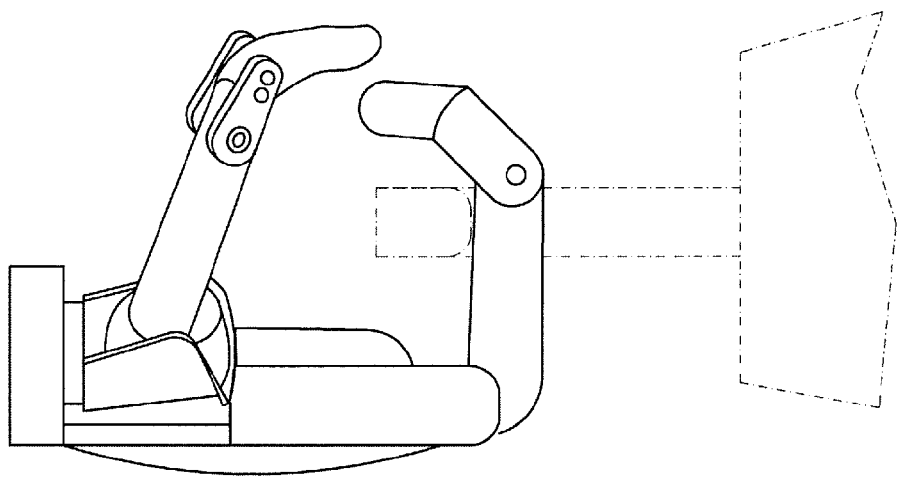
Figure 21A:
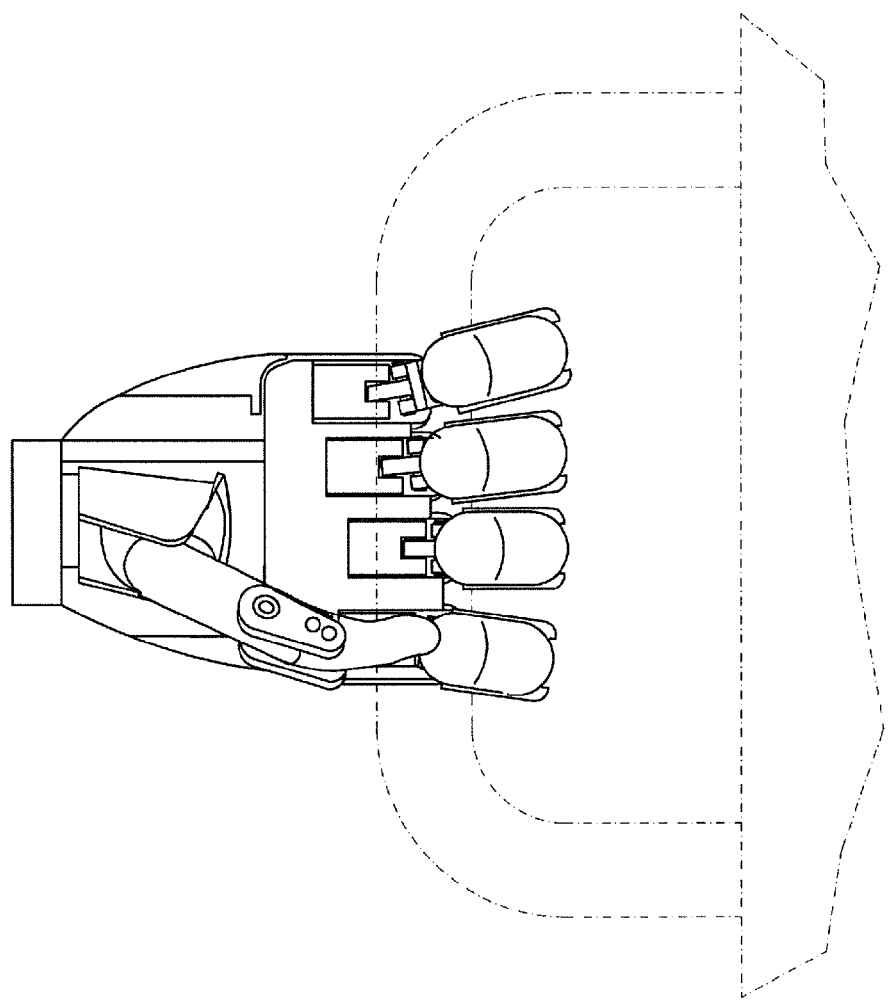

In another embodiment of the present invention, as is shown in FIGS. 19-21, "Position 4", or in other words a position that is most abducted towards the center of the palm is indicative of a desire by the user to attain a grip pattern for 1) gripping a cylindrical object or 3) grasping a pencil like object. Once the electronic control system receives the signal from the thumb sensor that the thumb is in Position 3, the system can determine that one of these positionings is required. If the user wants to use the device in this original position without any further movement or use of the other fingers, no additional input is necessary. If a different position is to be used, the electric control system 101 receives additional input form the patient sensors or other input mechanism. If the electronic control system receives input indicative of a cylindrical grip as shown in FIG. 20, the motor drive is activated to flex or extend all of the fingers simultaneously to take hold of the cylindrical object. In this positioning, the user is able to control the fingers for the release or grip of the water bottle or other cylindrically shaped object for example. Alternatively, if the inputs received from the patient sensor or other input device is to effectuate a hook grip from an abducted position, the electronic control system effectuates the motor drive to flex and/or extend all of the fingers at the same time. In this scenario, the thumb is directly in front of the other fingers as opposed to the abducted hook grip discussed above with regard to Position 1 where the thumb was extended away from the other fingers. In this positioning, the thumb acts move like a hook that is directly in front of the fingers performing the rest of the grip.

While there had been shown and described fundamental features of the invention as applied to being exemplary embodiments thereof, it will be understood that omissions and substitutions and changes in the form and details of the disclosed invention may be made by those skilled in the art without departing from the spirit of the invention. Moreover, the scope of the present invention covers conventionally known, future developed variations and modifications to the components described herein as would be understood by those skilled in the art. It is the intention, therefore, to be limited only as indicated by the scope of the claims appended hereto. It is also to be understood that the following claims are intended to cover all of the generic and specific features of the invention herein disclosed and all statements of the scope of the invention that, is a matter of language, might be said to fall there between.

We claim:

1. A device comprising:
   one or more patient sensors;
   a prosthetic device, wherein the prosthetic device comprises a palm member that forms a plane along the surface of the palm member and a center axis through the center of the plane, a thumb member, multiple finger members and an angle sensor that measures the position of the thumb member around an axis of rotation generally parallel to the center axis;
   a control system in communication with the one or more patient sensors and the angle sensor; and
   a driving mechanism in communication with the control system and connected to the prosthetic device;
   wherein the control system is configured to manipulate the driving mechanism to position one or more of the multiple finger members in response to the rotation of the thumb member along said axis of rotation as measured by the angle sensor and based upon the inputs received from the one or more patient sensors.

2. The device of claim 1 wherein the driving mechanism moves one or more of the multiple finger members towards the surface of the palm member.

3. The device of claim 1 wherein the driving mechanism moves one or more of the multiple finger members away from the surface of the palm member.

4. The device of claim 1 wherein the control system suspends movement of one or more of the multiple finger members.

5. A device comprising:
   one or more patient sensors for sensing an input from a patient;
   a prosthetic device, wherein the prosthetic device comprises a palm surface that forms a plane and has a center axis through the center of the plane, a thumb member, multiple finger members and an angle sensor that measures the position of the thumb member around an axis of rotation generally parallel to the center axis;
   a control system in communication with the one or more patient sensors and the angle sensor; and
   a driving mechanism in communication with the control system and connected to the prosthetic device;
   wherein the control system is configured to manipulate the driving mechanism to position one or more of the multiple finger members in response to the rotation of the thumb member along said axis of rotation as measured by the angle sensor and based upon the inputs received from the patient sensors.

6. The device of claim 5 wherein the patient sensor is an electromyographic sensor.

7. The device of claim 5 wherein the patient sensor is a force sensing resistor sensor.

8. The device of claim 5 wherein the patient sensor is a switch sensor.

9. The device of claim 5 wherein the input from the patient is a contraction or expansion of the patient's muscle.

10. The device of claim 5 wherein the driving mechanism moves one or more of the multiple finger members towards the surface of the palm member.

11. The device of claim 5 wherein the driving mechanism moves one or more of the multiple finger members away the surface of the palm member.

12. The device of claim 5 wherein the control system suspends movement of one or more of the multiple finger members.

13. A device comprising:
one or more patient sensors for sensing an input from a patient;
a prosthetic device, wherein the prosthetic device comprises a thumb member, multiple finger members and a palm member having a surface wherein the thumb member is rotatable from a first position to a second position;
an angle sensor that measures whether the thumb is in a first position or a second position; a control system in communication with the one or more patient sensors and the angle sensor and
a driving mechanism in communication with the control system and connected to the prosthetic device;
wherein the first position and the second position are along a generally horizontal plane relative to the center of the surface of the palm member and the control system is configured to manipulate the driving mechanism to position one or more of the multiple finger members based upon the inputs received from the one or more patient sensor and in response to the thumb member being rotated from the first position to the second position as said rotation is measured by the angle sensor.

14. The device of claim 13 wherein the patient sensor is an electromyographic sensor.

15. The device of claim 13 wherein the patient sensor is a force sensing resistor sensor.

16. The device of claim 13 wherein the patient sensor is a switch sensor.

17. The device of claim 13 wherein the input from the patient is a contraction or expansion of the patient's muscle.

18. The device of claim 13 wherein the driving mechanism moves one or more of the multiple finger members away from the surface of the palm member.

19. The device of claim 13 wherein the driving mechanism moves one or more of the multiple finger members towards the surface of the palm member.

20. The device of claim 13 wherein the control system suspends movement of one or more of the multiple finger members.

* * * * *